United States Patent
Hodges et al.

[11] Patent Number: 5,562,121
[45] Date of Patent: Oct. 8, 1996

[54] GAS DELIVERY SYSTEM WITH UNIVERSAL OUTLET

[75] Inventors: Steven M. Hodges, St. Charles; Dennis A. Dohogne, St. Peters, both of Mo.

[73] Assignee: Allied Healthcare Products, Inc., St. Louis, Mo.

[21] Appl. No.: 417,671

[22] Filed: Apr. 6, 1995

[51] Int. Cl.⁶ .................................................. F16L 5/00
[52] U.S. Cl. ................. 137/360; 137/614.05; 285/24; 285/64; 285/308; 285/317; 285/914
[58] Field of Search ............................. 285/12, 317, 308, 285/192, 914, 24, 25, 26, 27, 28, 29, 64; 137/360, 614.05

[56] References Cited

U.S. PATENT DOCUMENTS

| | | |
|---|---|---|
| 2,905,487 | 9/1959 | Schifter . |
| 3,003,213 | 10/1961 | Rogers ............................... 285/192 X |
| 3,287,031 | 11/1966 | Simmons et al. ..................... 285/914 X |
| 3,448,760 | 6/1969 | Cranage . |
| 3,563,267 | 2/1971 | Thompson . |
| 3,643,985 | 2/1972 | Cranage ................................. 285/317 |
| 3,776,272 | 12/1973 | Arbon . |
| 3,931,829 | 1/1976 | McWhinnie, Jr. et al. . |
| 4,150,673 | 4/1979 | Watt ..................................... 285/914 X |
| 4,190,075 | 2/1980 | Kayser . |
| 4,290,853 | 9/1981 | Gigou . |
| 4,344,455 | 8/1982 | Norton et al. . |
| 4,354,523 | 10/1982 | Hochmuth et al. . |
| 4,509,554 | 4/1985 | Failla . |
| 4,527,587 | 7/1985 | Fairlamb . |
| 4,562,856 | 1/1986 | Garvey et al. . |
| 4,572,232 | 2/1986 | Gruber . |
| 4,591,298 | 5/1986 | Fukumori et al. . |
| 4,617,012 | 10/1986 | Vaillancourt . |
| 4,683,905 | 8/1987 | Vigneau et al. . |
| 4,718,699 | 1/1988 | Kulish et al. ............................. 285/12 |
| 4,774,939 | 10/1988 | Disney . |
| 4,790,567 | 12/1988 | Kawano et al. ..................... 285/914 X |
| 4,844,409 | 7/1989 | Lackler et al. .......................... 285/308 |
| 4,915,132 | 4/1990 | Hodge et al. . |
| 5,129,423 | 7/1992 | Fournier et al. . |
| 5,131,429 | 7/1992 | Nixon . |
| 5,197,511 | 3/1993 | Kohn et al. . |
| 5,217,203 | 6/1993 | Cattini . |
| 5,236,005 | 8/1993 | Berg . |
| 5,293,913 | 3/1994 | Preszler . |
| 5,333,644 | 8/1994 | Heyden et al. . |
| 5,353,837 | 10/1994 | Faust . |
| 5,368,065 | 11/1994 | Humpert et al. . |

FOREIGN PATENT DOCUMENTS 2625545 7/1989 France ................................. 285/914

*Primary Examiner*—Dave W. Arola
*Attorney, Agent, or Firm*—Dickstein, Shapiro & Morin LLP

[57] ABSTRACT

A gas outlet system that includes a first indexing structure mating with a first adaptor for releasably connecting the first adaptor to the outlet, and a second indexing structure mating with a second adaptor for releasably connecting the second adaptor to the outlet. The gas outlet system includes an engaging member for engaging the adaptor to the outlet and includes first and second urging members each independently operable to disengage the engaging member to release the adaptor.

15 Claims, 7 Drawing Sheets

GAS DELIVERY SYSTEM WITH UNIVERSAL OUTLET

BACKGROUND

The present invention relates to systems for delivering gases. More particularly, the invention relates to a system employing a gas-specific outlet that is keyed to a same gas-specific adaptor.

Pressurized gas supply networks are known for providing a gas outlet station with a gas. A detachable adaptor mates with the outlet for establishing the gas flow under pressure from a gas supply outlet to secondary equipment for ultimate use of the gas.

For example, in medical treatment environments, such as hospitals, it is commonplace to have available wall or ceiling mounted gas outlet stations for supplying gases such as nitrogen, carbon dioxide, air, oxygen or nitrous oxide. The outlet station typically may be mounted together with a face plate assembly and a mounting box which is permanently installed in the wall or ceiling of the treatment area and to which a gas supply conduit is routed. The outlets stations are supplied by a permanently installed gas supply system connected to corresponding gas storage tanks or pumps which may be quite remote from any area of ultimate use of the gas. Such outlet stations may also include a vacuum or suction line service connection or other desirable gaseous fluid flow service connections.

For each different gas or service available at an outlet station, the outlet station commonly includes an adaptor connection assembly which is opened when connected with the proper adaptor to deliver gas via the adaptor to the connected secondary equipment or user, and is closed leak-tight when the adaptor is disconnected to preclude leakage of pressurized gas from the system into the ambient air of the hospital room.

Gas supply systems are known which provide schemes of non-redundant keying to ensure error free gas access. In such systems, the outlet and the adaptor are keyed together according to the gas type. Also, the outlet and the adaptor are clearly marked with their gas type, so the user can easily read the markings. Because of the keying, an oxygen outlet will only mate with an oxygen adaptor. The nitrogen, air, vacuum, or other gas adaptors will not fit into the oxygen outlet. Thus, oxygen cannot be supplied by mistake through an adaptor of the wrong gas type. In this same way each of the gas types have a corresponding uniquely configured outlet and mating adaptor.

Two known types of outlet to adaptor keying are the "Diameter Indexed Safety System" (DISS) and the "Quick Connection System" (QC). In DISS, the gas outlet valves for each of a plurality of different gases or services include unique diameters which differ from the diameters of outlet valves for all other gases. Accordingly, only the adaptors for the same gas type which have mating diameter plugs fit each such outlet valve.

In a QC system, each adaptor includes an elongated valve plug which is sized to engage with a matching outlet valve aperture. The engagement opens the valve and establishes a leak tight gas flow connection through the plug and adaptor to the secondary equipment and the user. The connection is secured or latched by a latch mechanism.

In one known type of QC system, the latch mechanism is separate from the valve plug. A latching pin is disposed in spaced parallel relationship with the elongated valve plug. When the adaptor is plugged in, the latching pin enters an aperture on the outlet and is engaged by a mechanism to hold the adaptor to the outlet. The latching pin has a cross-sectional shape, such as round or square, or other shape. The aperture provided in the outlet for accepting the latching pin has a matching shape. The spacing between the plug and latching pin in combination with the cross-sectional shape of the latching pin defines a keyed relationship such that each adaptor is engagable only with an outlet station of the same gas type. Such a system is described in U.S. Pat. No. 4,718,699, the disclosure of which is incorporated herein by reference.

In another type of QC system, the latch mechanism includes the valve plug and no separate latching pin is used. For keying, recesses are provided on the outlet at selected locations spaced around the aperture for receiving the valve plug. Corresponding pins are provided on the adaptor for mating with the recesses when the adaptor is plugged into the outlet. Each gas type has a unique pin and recess placement, so that only adaptors and outlets of matching gas types can be used together. Such a system is described in U.S. Pat. Nos. 4,844,409 and 3,563,267, the disclosure of which is incorporated herein by reference.

Just as proper adaptor-to-outlet station connections are of critical importance in medical gas supply systems, so too are proper matching of the various outlet station valves, face plates and latching assemblies to the permanently installed mounting box and the gas supply conduit associated therewith. The potential severity of the consequences of improper outlet station assembly is of such magnitude as to dictate a very high standard of care. Accordingly, non-redundant keying schemes are also known in the art for keying outlet valves or mounting boxes, and the like, in order to ensure error free assembly of the various outlet station components during system installation.

The prior art includes numerous examples of gas outlet station valve assemblies and cooperating adaptors, of which the following are exemplary: U.S. Pat. Nos. 2,905,487, 3,448,760, 3,563,267, 4,718,669, and 4,844,409.

Certain shortcomings of the prior art have been noted. Conventionally, different manufacturers of adaptors and medical gas outlets employ different keying structure for matching outlets for a specific gas to the corresponding adaptor for the same gas. Therefore, an adaptor made by one manufacturer does not fit into an outlet made by another manufacturer. Thus the existence of different adaptor connecting systems has resulted in distinct and mutually incompatible outlet station constructions thus limiting the choice of components in gas supply system design.

In view of the above-described deficiencies in the art there is a need for a device which accepts differently shaped adaptors for a given medical gas service.

SUMMARY

The present invention alleviates to a great extent the problems of the prior art by providing a gas outlet system that includes a first indexing structure mating with a first adaptor for releasably connecting the first adaptor to the outlet, and a second indexing structure mating with a second adaptor for releasably connecting the second adaptor to the outlet.

In one aspect of the present invention, the gas outlet system includes an engaging member for engaging the adaptor to the outlet and further includes first and second urging members, each independently operable to disengage the engaging member to release at least one type of adaptor.

It is an object of the invention to provide a medical gas outlet system which includes more than one type of adaptor.

It is a further object of the invention to provide a medical gas outlet system having the foregoing advantages and in which each adaptor can be releasably connected to the outlet of the system in the same manner that the adaptor is releasably connected to an outlet of its own type.

It is another object of the invention to provide a medical gas outlet having the foregoing advantages and in which, for at least one type of adapter, includes more than one way of releasing the adaptor.

The above and other objects, advantages and features of the invention will be more readily understood from the following detailed description of the invention which is provided in connection with the accompanying drawings.

DETAILED DESCRIPTION OF A PREFERRED EMBODIMENT

Figure 2:
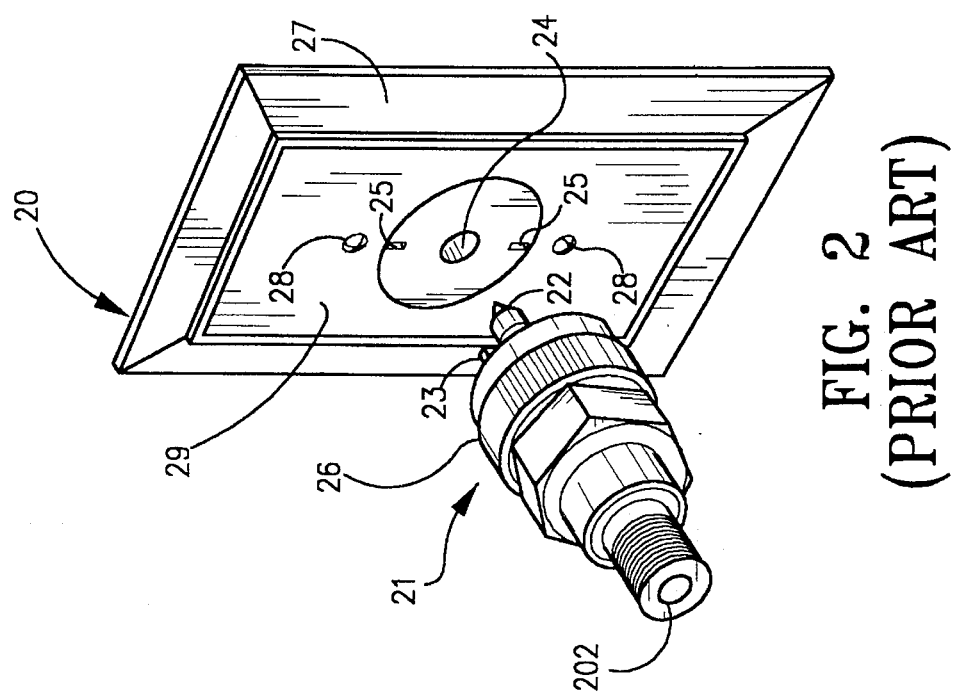
FIG. 2 is a perspective view of a second type of prior art medical gas outlet and adaptor.
Figure 1:
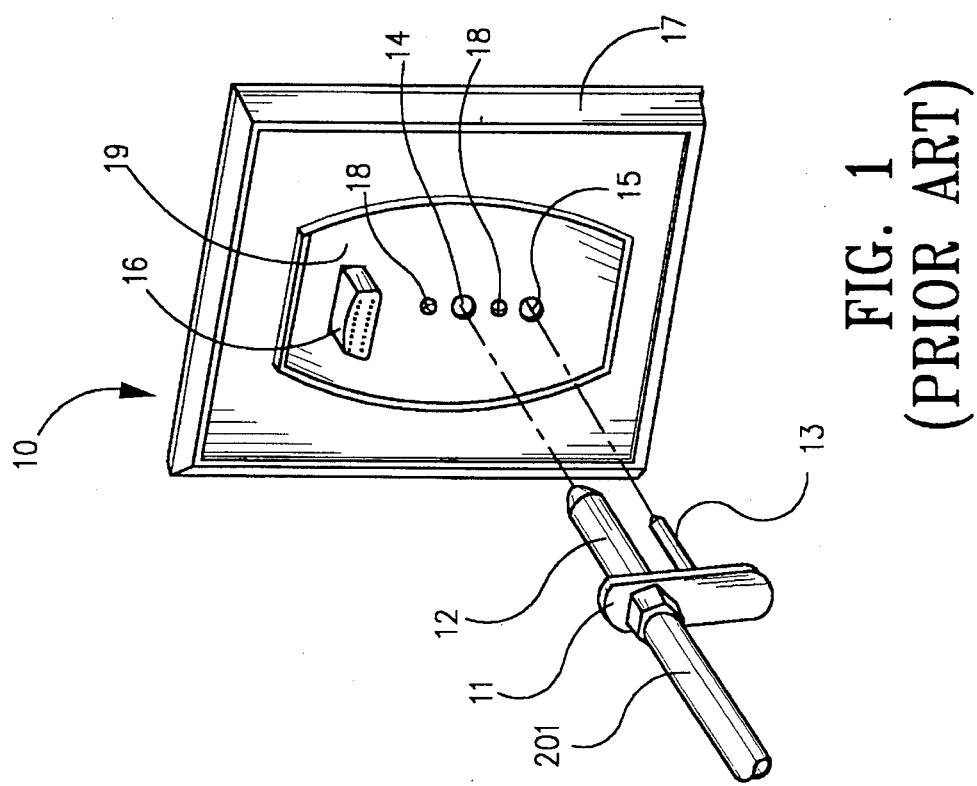
FIG. 1 is a perspective view of a first type of prior art medical gas outlet and adaptor.

Refer now to FIGS. 1 and 2, there being shown two types of prior art outlet systems. In a first type of known medical gas outlet system 10, as shown in FIG. 1, and as described in U.S. Pat. No. 4,718,699, an adaptor 11 has a valve plug 12 and an adaptor latch pin 13. The adaptor 11 is inserted into the outlet 10, through a valve opening 14 and a latch pin receiving opening 15. The outlet 10 includes a facia plate 17 connected to a cover plate 19. The cover plate 19 and facia plate 17 are attached to the outlet 10 with two screws 18. A push-to-release button 16 extends through the cover plate 19 for releasing the adaptor 11. The outlet 10 also includes a spring latch (not shown) adapted to releasably retain the adaptor latch pin 13. The adaptor 11 includes gas-specific adaptor-indexing structure mating with the outlet-indexing structure of an outlet 10 of the same gas type. The latch pin receiving opening 15 has a cross-sectional geometry and a spacing from the valve opening 14 that is unique to a specific gas and matches the adaptor 11 of the same gas type so that a user cannot inadvertently plug, for example, an oxygen adapter into a nitrogen outlet. After the adaptor 11 is engaged by the spring latch, gas can flow through the outlet 10, through the plug 12 and gas supply conduit 201 to the secondary equipment and the end user. The adaptor 11 may be released by operating the push-to-release button 16 which operates the spring latch.

FIG. 2 shows a second type of known outlet system 20, as described in U.S. Pat. No. 4,844,409. An adaptor 21 plugs into the outlet 20. The outlet 20 includes a face plate 29 covering a facia plate 27, both of which are secured by screws 28 to the outlet 20. The adaptor 21 has an elongated nose 22 dimensioned to fit within a center aperture 24 of the outlet 20. The elongated nose 22 is sealed within the outlet 20 by an O-ring (not shown) to provide a leakfree flow of gas. The adaptor 21 has an enlarged release knob 26. The adaptor 21 includes gas-specific adaptor-indexing structure mating with the outlet-indexing structure of an outlet 20 of the same gas type. A pair of keying lugs 23 extend from the face of the knob 26 towards the facia 27 and fit into a pair of corresponding keying cavities 25 located on the outlet 20. By selecting positions for the keying lugs 23 and keying cavities 25 that are unique for each gas, it can be assured that only the same gas adaptors can be operatively used with outlets for that gas. The release knob 26 can be rotated with respect to the adaptor 21, for moving between a first position where the adaptor 21 is secured within the outlet 20, and a second position where the adaptor is released from the outlet 20. The release knob 26 is spring biased (not shown) toward its first position. When the adaptor 21 is inserted into the outlet 20, the legs of a hairpin shaped spring (not shown) engage flats (not shown) formed in the nose 22 to prevent the adaptor 21 from being removed from the outlet 20. To release the adaptor 21 from the outlet 20, the release knob 26 is manually rotated by a user until it reaches its second position. With this rotation, the flats are rotated out of engagement of the legs of the spring and the legs of the spring are spread out to be the same as the diameter of the elongated nose 22. The adaptor 21 may then be withdrawn from the outlet 20.

Figure 3:
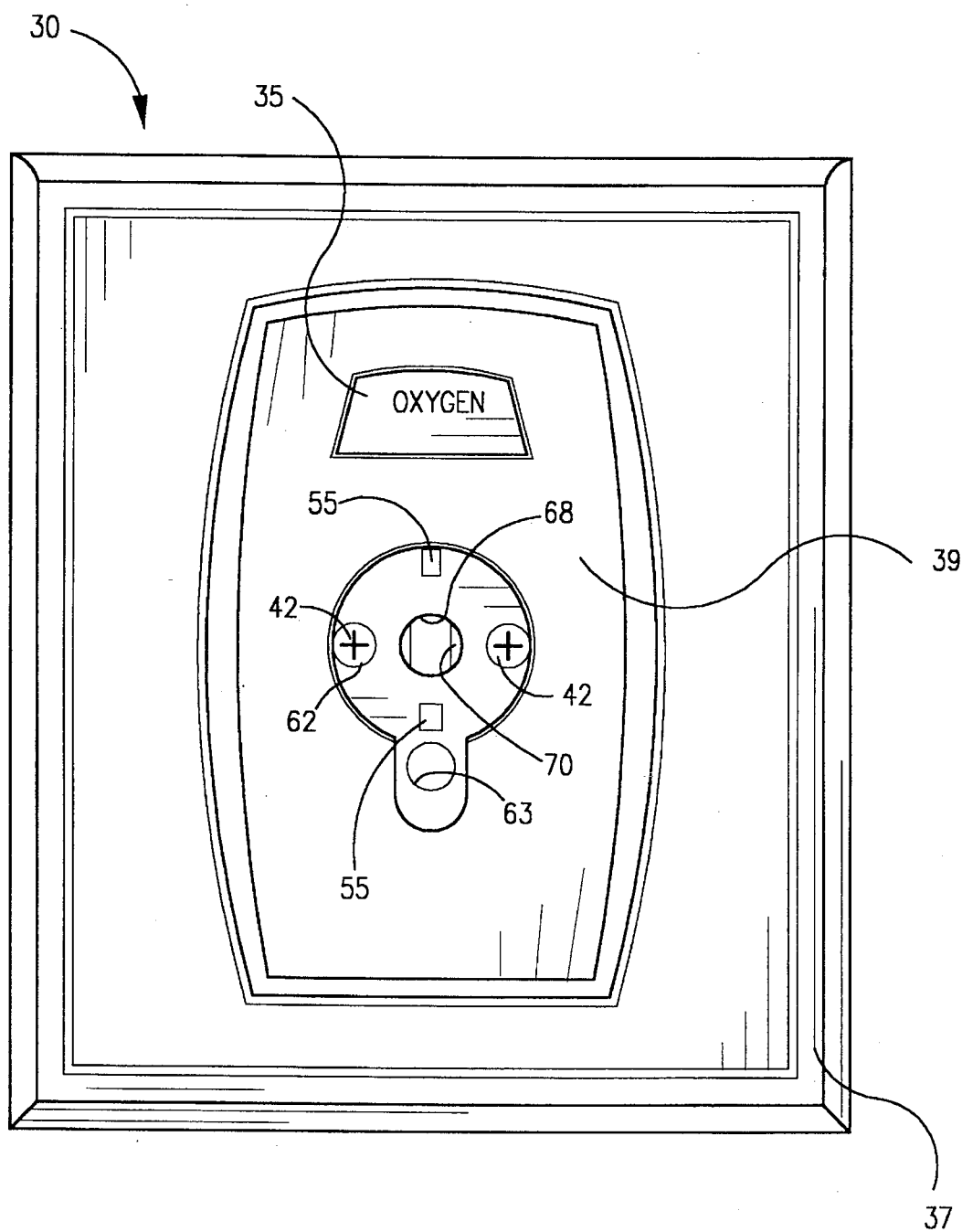
FIG. 3 is a front view of a preferred embodiment of the present invention.

Refer now to FIG. 3, there being shown an outlet system, generally designated by reference numeral 30, according to a preferred embodiment of the present invention. The outlet system 30 is adapted to accommodate both types of the adaptors 11 and 21 shown in FIGS. 1 and 2. The outlet system 30 includes valve aperture 68 and a latch pin receiving aperture 63 for receiving the adaptor 11. Thus the adaptor 11 would utilize valve aperture 68 and latch pin receiving aperture 63, whereas the adaptor 21 would utilize keying cavities 55 and valve aperture 68. Once engaged, release button 35 is pushed to release either the adaptors 11 and 21 from the outlet assembly 30 in a manner further discussed below. Alternatively, the adaptor 21 may be released by rotating release knob 26 to disengage hairpin shaped spring 70. Screws 42 connect together the portion of the outlet system 30 as discussed further below.

Figure 4:
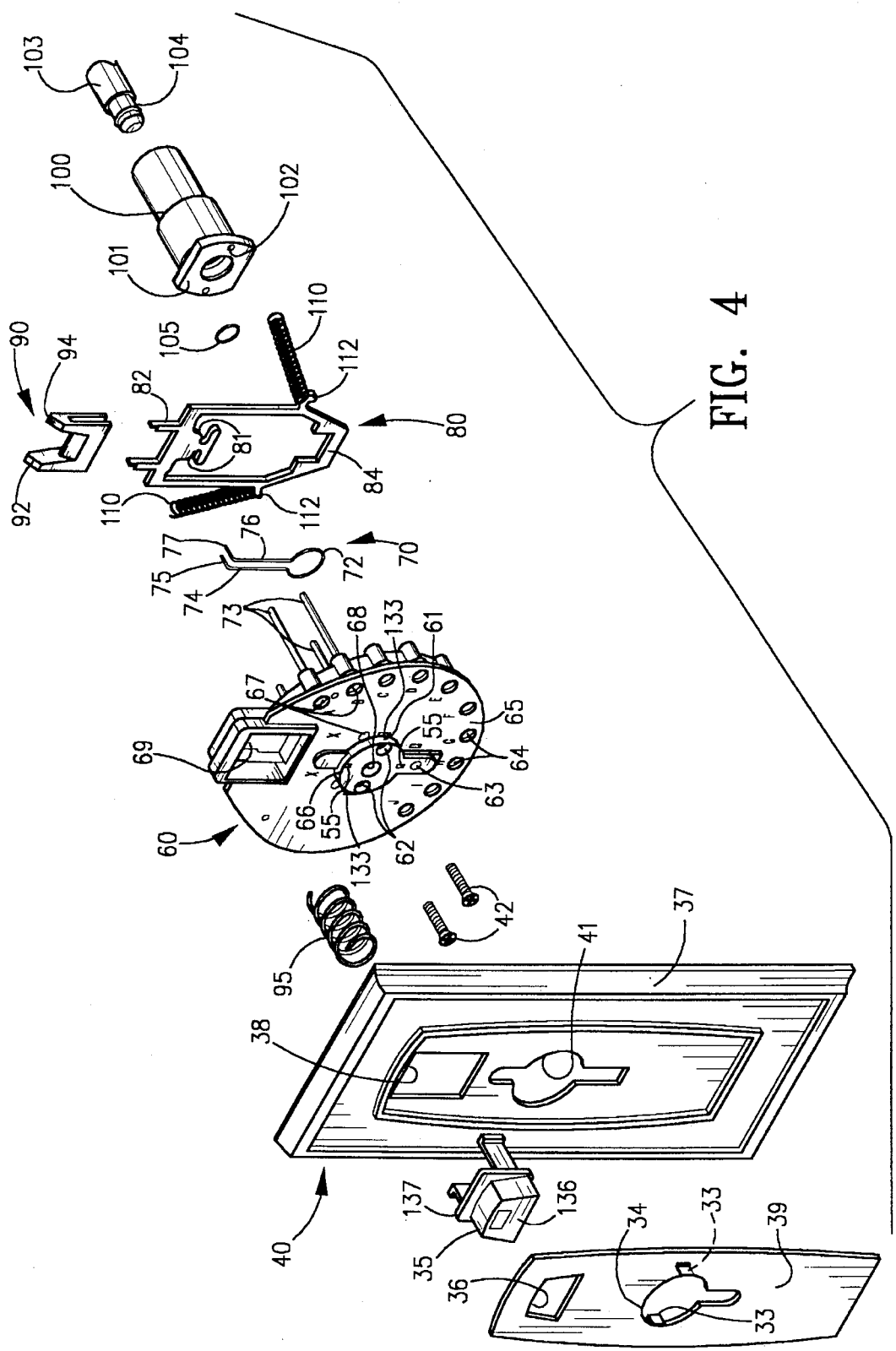
FIG. 4 is an exploded perspective view of the outlet of FIG. 3.

Refer now to FIG. 4 which shows an exploded view of a portion of the outlet system 30 of FIG. 3. The outlet system 30 is constructed similar to the system described in U.S. Pat. No. 4,718,699 except with regard to the adaptor keying and latching structure which is described herein. The outlet system 30 includes a face plate assembly 40, and an index plate assembly 60. The face plate assembly 40 includes a facia plate 37 and a cover plate 39. The cover plate 39 includes a button aperture 36 and a key opening 34. A pair of tabs 33 extend rearwardly from the plate 39 to extend through a pair of slots 133 of the index plate assembly. The tabs 33 are designed to hold the face plate assembly 40 to the index plate assembly 60. The plate 37 has a button opening 38 and a key opening 41, corresponding to the button opening 36 and the key opening 34, respectively, of the cover plate 39. A release button 35 extends through the button opening 36 and the corresponding button opening 38. The opening 36 is sized to allow the head 136 of the button 35 to protrude from the plate 39 and to block the shoulder 137 of the button 35 to hold the shoulder behind the plate 39.

The index plate assembly 60 includes a plate 65 with collars 64 through which a number of indexing pins 73 extend. The pins 73 have enlarged heads 67 that engage and are held by the plate 65. An index portion 66 is integrally formed with plate 65 to extend out from the front of plate 65. The portion 66 defines the general area in which the keying cavities and apertures are formed for accepting the corresponding keying features on the adapters. The index portion 66 includes the pair of keying cavities 55, the center opening 68, and the latch pin receiving aperture 63, for mating with the adaptors 11 and 21. A window 69 is formed through the plate 65 for receiving and guiding the release button 35, against the force of spring 95. The back of the index plate assembly 60 includes pins 73 positioned at locations unique to a specific type of gas for keying to the outlet box (not shown), as described in U.S. Pat. No. 4,718,699.

A hairpin shaped spring 70 is connected to the back face of index plate assembly 60. The hairpin shaped spring 70 includes a head portion 72, legs 74 and 76 extending from the head, and feet 75 and 77 extending from the legs. The legs 74 and 76 are engaging members that engage the flat portions of the adaptor 21 to latch the adaptor 21 to the outlet 30. A latch frame 80 is also mounted to the back of the index plate assembly 60. The latch frame 80 has a latch bar 84 which is an engaging member that is positioned to engage the latch pin 13 of the adaptor 11. A latch release member 90 fits over and engages latch release engaging portion 82, to move latch 80 in a downward direction when the button 35 is pushed. The latch frame 80 includes a pair of cams 81 positioned to bear on the feet portions 75 and 77 to urge the feet 75 and 77 and thus the legs 74 and 76 out of engagement with the flats of the nose of the adaptor 21. Finally, a valve 100 has a flange portion 101 which is affixed to the back of the index plate assembly 60 by screwing the screws 42 into the screw holes 62 of the index plate assembly 60 and into the opening 102 of the valve 100. A valve O-ring 105 is inserted into one end of valve 100 to seal the valve plug 12 of the adaptor 11. Also, a poppet 103 with an O-ring 104 is inserted into the other end of valve 100, similar to conventional arrangements for valves of this type.

Figure 6:
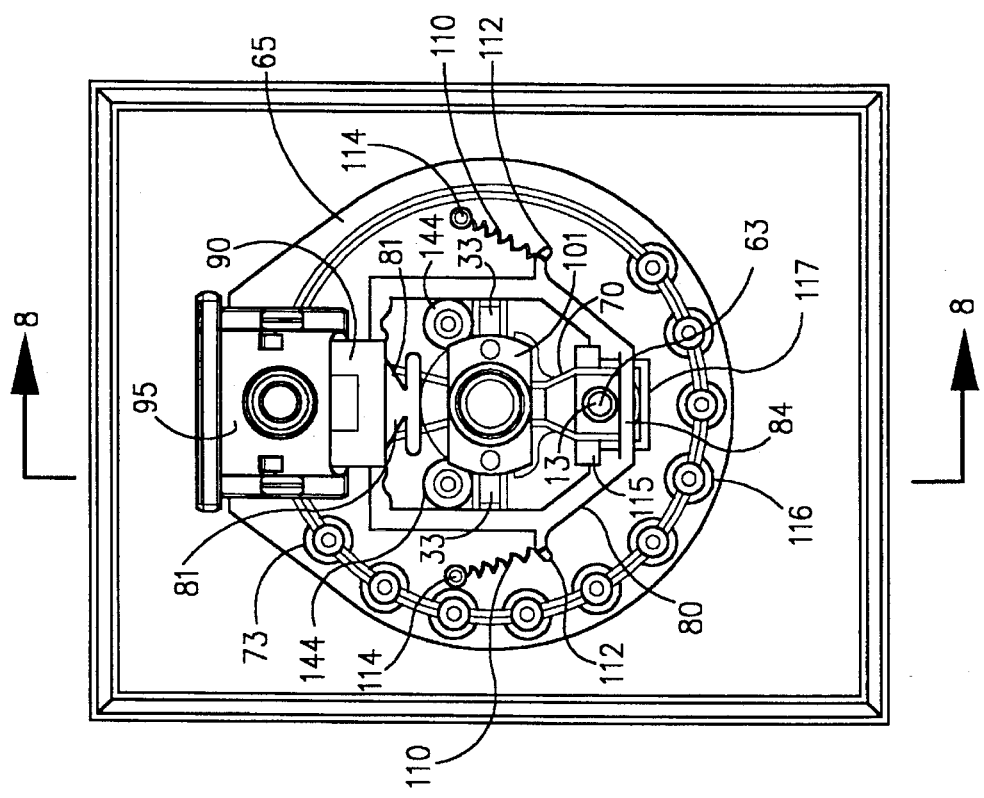
FIG. 6 is a view like FIG. 5 in a releasing position.
Figure 5:
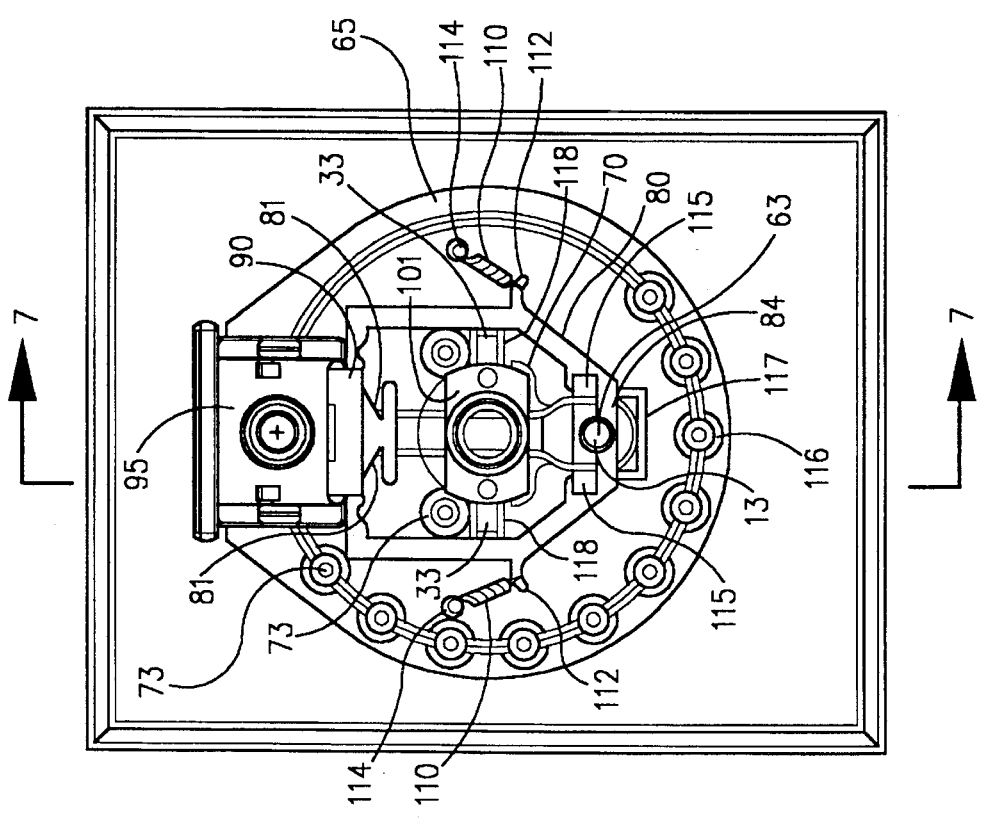
FIG. 5 is a rear view of the outlet of FIG. 3 in an engaged position.
Figure 7:
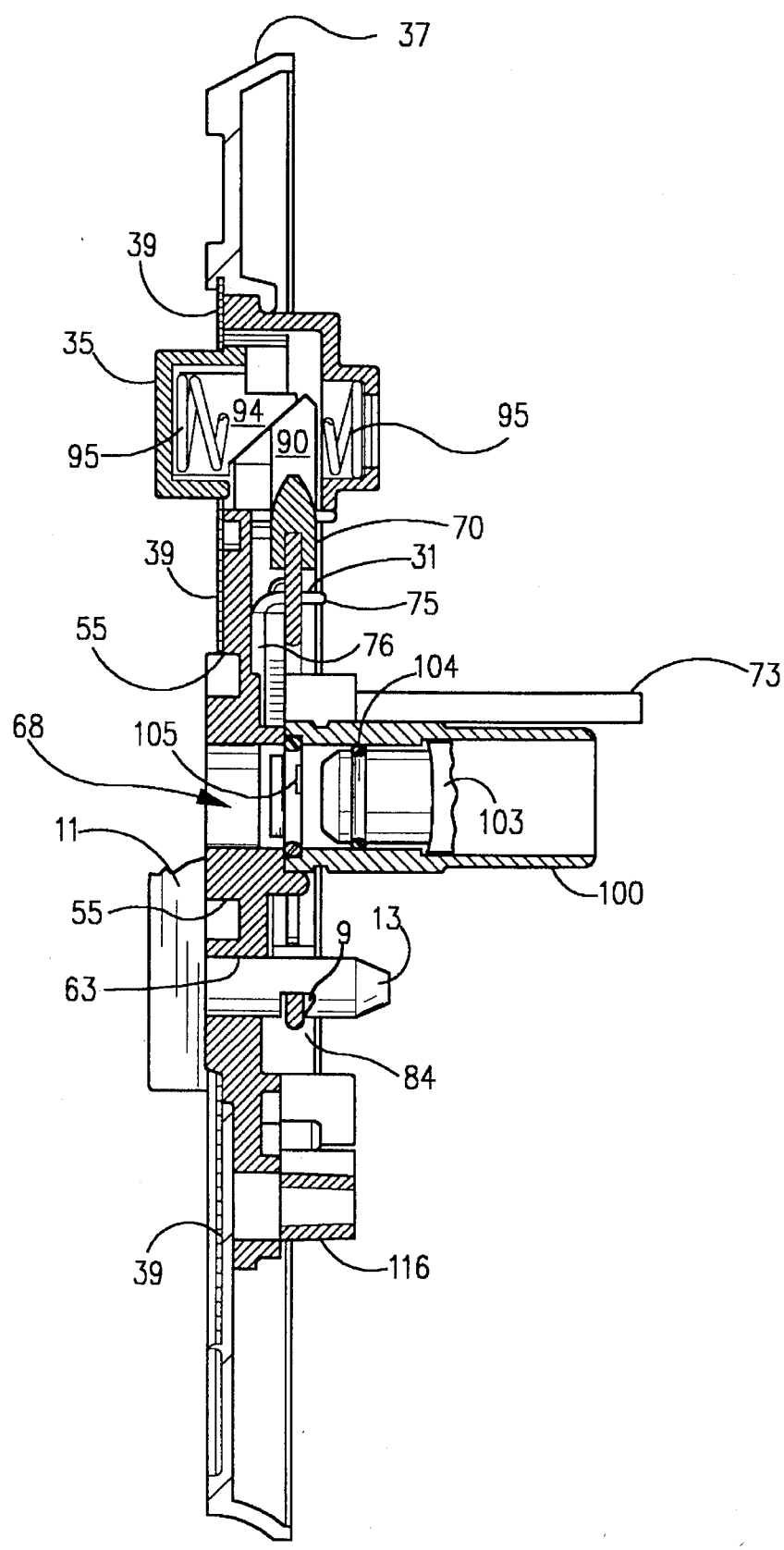
FIG. 7 is a cross-sectional view taken along section line VII—VII of FIG. 5.
Figure 8:
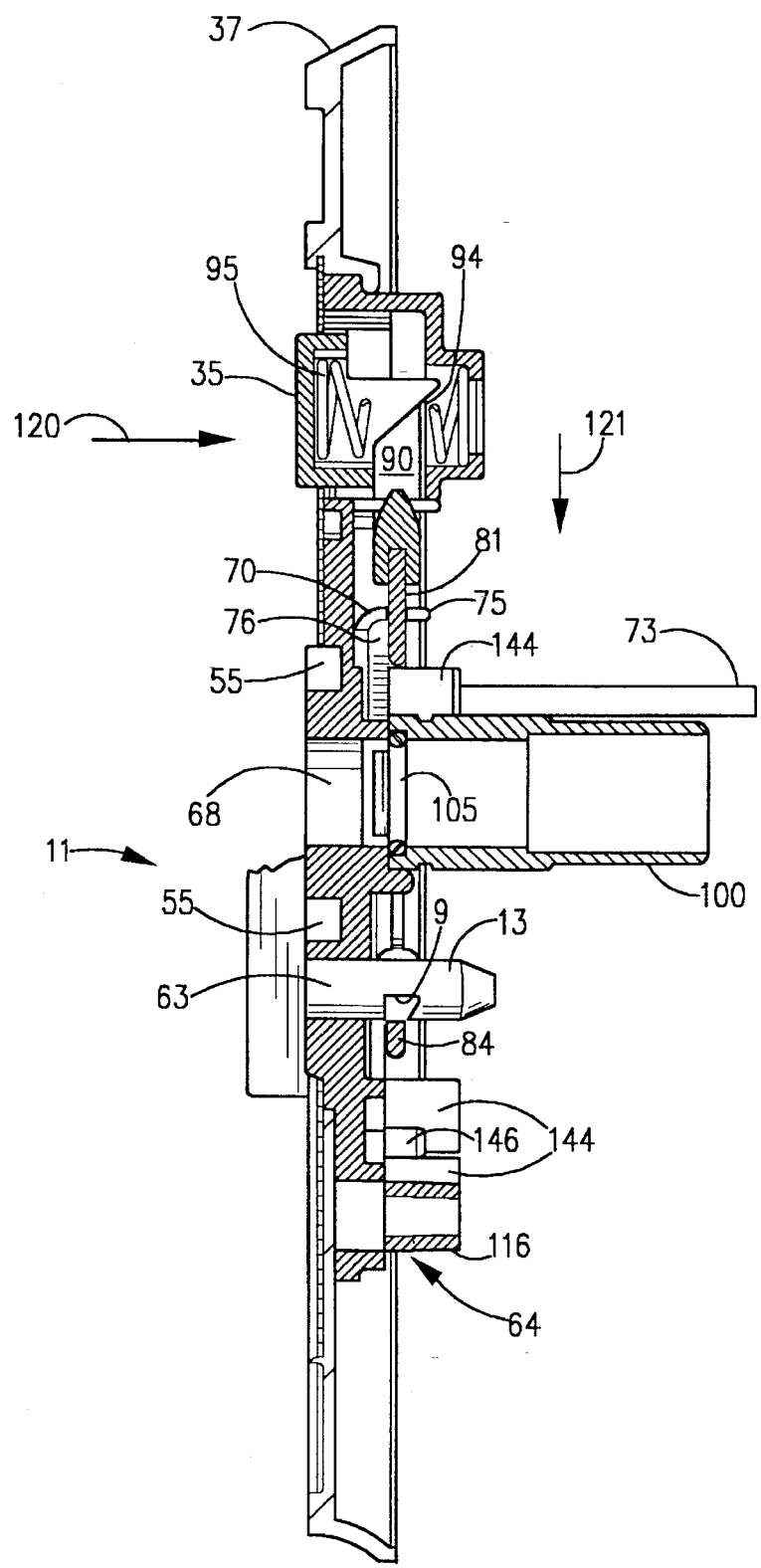
FIG. 8 is a cross-sectional view taken along section line VIII—VIII of FIG. 6.

FIGS. 5 and 6 show the latch frame 80 mounted on the back of the index plate 65 in an engaged position and in a releasing position, respectively. FIGS. 7 and 8 show cross-sectional views of FIGS. 5 and 6, respectively. In FIGS. 5 and 7, hairpin shaped spring 70 and the latch bar 84 are in engaged positions to engage the adaptors 11 and 21. In FIGS. 6 and 8, the latch bar 84 and the hairpin shaped spring 70 are in a releasing position, so as to release the adaptors 11 and 21. For illustrative purposes, FIGS. 7 and 8 show the adaptor 11 inserted into latch pin receiving aperture 63, as the latch frame 80 is moved from an engaged position to a releasing position, respectively. The adaptor plug 12 is present, but is not shown in the FIGS. The poppet 103 is urged by a spring (not shown) towards the front and is shown in FIG. 7 in the sealed, or closed position, with poppet O-ring 105 engaging the small inside diameter portion of the valve 100. Also shown in FIGS. 5 and 6 are tabs 33 extending through the apertures 133 and bent over to lay in the recesses of the tab seats 118 to inhibit tampering with and disengagement of the tabs 33.

Figure 9:
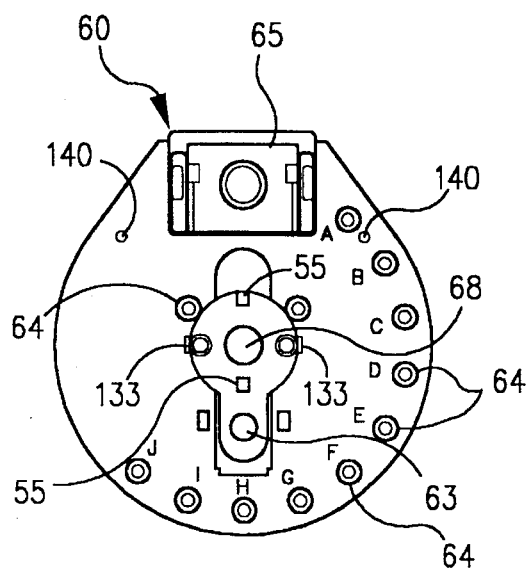
FIG. 9 is a front view of the index plate of the outlet of FIG. 3.
Figure 10:
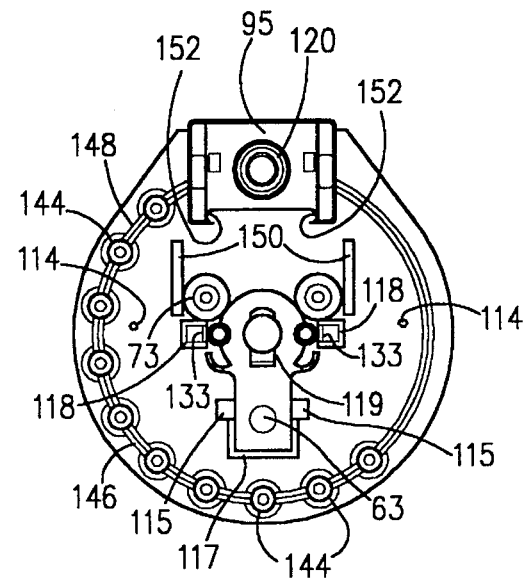
FIG. 10 is a back view of the index plate of FIG. 9 without the engaging members.
Figure 11:
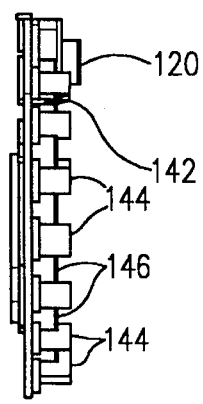
FIG. 11 is a side view of the index plate of FIG. 9.

As shown in FIGS. 5 through 8, to engage and release the adaptor 11 of FIG. 1, the latch bar 84 of the latch frame 80 is moved in and out of engagement with the latch pin 13 of the adaptor 11. As the latch pin 13 is inserted through the receiving aperture 63, it urges upon the latch bar 84 and pushes the frame 80 down against the spring force of the return springs 110. The springs 110 are each hooked in tension at one end to an ear 112 of the frame 80 and at the other end to a pin 114. Alternatively, each of springs 110 could be hooked into holes 142 (FIG. 11) formed by extending holes 140 (FIG. 9) through the plate 65 and into the webs 146 between the bosses 144 of the collar 64. Movement downward of the frame 80 also angularly spreads the spring 70 by action of the cams 81, urging the spring 70 out of engagement with the adaptor 21. Upon full insertion, as shown in FIG. 8, a recess 9 on the latch pin 13 allows the latch bar 84 to return to the latched position thus engaging the recess 9 of the latch pin 13 to hold the adaptor 11 to the outlet 30 (as shown in FIG. 7). The adaptor 11 is released by pushing in the release button 35, which operates the spring latch. As the release button 35 is pushed in by a user, against the force of spring 95, in a direction indicated by the arrow 120 in FIG. 8, the release member 90 is urged and pushed down. The member 90 pushes down the latch frame 80 (as shown by arrow 121 in FIG. 8) thereby moving latch bar 84 down, out of engagement with the recess 9 of the latch pin 13, as shown in FIG. 9. The adaptor 11 may then be withdrawn from the outlet 30. After the adaptor 11 is withdrawn, the force of spring 95, as well as springs 110, returns the release button 35 toward its original position, prior to being pushed in.

To engage the adaptor 21 of FIG. 2, the elongated nose 22 of the adaptor 21 fits within the center opening 68. When the adaptor 21 is inserted into the outlet assembly 30, the legs 74 and 76 of the hairpin shaped spring 70 engage the flat portions on the nose 22. This locks the adaptor 21 to the outlet 30. To release the adaptor 21 from the outlet assembly 30, the release knob 26 is manually rotated clockwise or counter clockwise by a user until it reaches its second position. At this point, the legs 74 and 76 of spring 70 are urged by the full diameter of the nose 22 to spread out, as shown in FIG. 6, and the adaptor 21 may be removed from outlet assembly 30. Alternatively, the adaptor 21 may be released from the outlet assembly 30 by operating release button 35. As release button 35 is pushed in by a user, as described above, the cams 81 are pushed down, thereby spreading the legs 74 and 76 of the hairpin shaped spring 70 so that the adaptor 21 may be withdrawn from the outlet assembly 30. Again, after the adaptor 21 is withdrawn, the force of the spring 95 returns the release button to its original position.

Refer now to FIGS. 9 through 12 which show additional views of the index plate 60 without the latch mechanisms and the hairpin shaped spring mounted. The index portion 66 is specific to a single gas. The keying cavities 55 are positioned at locations around aperture 68 specific to that gas. The location shown in FIG. 9, i.e., top (zero degrees) and bottom (180 degrees) may correspond for example to oxygen. Recesses located at zero degrees, 150 degrees and 210 degrees may correspond to vacuum. The recesses may be shaped round, rectangular or other shape to uniquely accept only a corresponding profile of pin on the adaptor 21.

Figure 12:
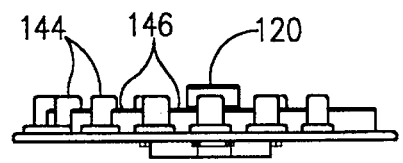
FIG. 12 is a bottom view of the index plate of FIG. 9.

Also shown are support and guide structures for the latch frame 80, the hairpin shaped spring 70, the release member 90 and the release button 35. This structure positions these components for operation as described above. In the engaged position as shown in FIGS. 5 and 7, the latch bar 84 of frame 80 is held in place from moving rearwardly and laterally by the latch stop tabs 115, which extend rearwardly from the back of the plate 65 and then turn outwardly to hook over and engage the frame 80. Frame 80 is held in place from moving forwardly by the runners 150 and from moving laterally by the guides 152 formed by the sides of the window 69. As the release button 35 is pushed in to release the adaptor 11, frame 80 moves downward guided by the tabs 115, the tab seats 118 and the center pin bosses 144, as shown in FIGS. 6 and 12.

Similarly, the movement of the hairpin shaped spring 70 is guided by spring keeper 117 and latch stop tabs 115, as shown in FIGS. 5 and 6. The spring stop 119 sets the positions of the legs 74 and 76 of hairpin shaped spring 70, limiting the inward movement of legs 74 and 76 in the engaged position, as shown in FIG. 5.

The above description and drawings are only illustrative of a preferred embodiment which achieves the objects, features and advantages of the present invention, and it is not intended that the present invention be limited thereto. Any modification of the present invention which comes within the spirit and scope of the following claims is considered part of the present invention. For example, although the outlet system is illustrated in a preferred embodiment as accommodating two types of adapters, more than two types could be accommodated within the scope of the invention. Also, combinations of types of adapters in addition to or other than the two described could be accommodated by an outlet system according to the invention.

What is claimed as new and desired to be protected by Letters Patent of the United States is:

1. A medical gas outlet system for delivering a medical gas from a supply of the gas according to at least two different non-redundant keying schemes, wherein the first non-redundant keying scheme has a plurality of first adapter types keyed to corresponding specific gas types, each of the first adapters including a valve nose through which the medical gas is received, and including a first gas-specific type of keying structure unique to a corresponding specific gas, and wherein the second non-redundant keying scheme has a plurality of second adapter types keyed to corresponding specific gas types, each of the second adapters including a valve nose through which the medical gas is received, and including a second gas-specific type of keying structure unique to a corresponding specific gas and different from the first type of gas-specific keying structure, said outlet system comprising:

a valve aperture sized to accept the valve nose of the first or second adapters and to guide the nose into engagement with a gas valve, said valve aperture being opened by engaging with the nose;

a first gas-specific outlet-indexing structure to mate with the first gas-specific adapter keying structure to permit the nose of the plurality of adapters of the first non-redundant keying scheme of the corresponding gas to be inserted into said valve aperture;

a second gas-specific outlet-indexing structure to mate with the second gas-specific adapter keying structure to permit the nose of the plurality of adapters of the second non-redundant keying scheme to be inserted into said valve aperture; and a seal positioned to inhibit the medical gas from leaking when the gas flows from the gas supply to the nose of the first or second adapter types.

2. The medical gas outlet system of claim 1 in which the first and second gas-specific keying structures each include at least one keying pin, wherein said first and second gas-specific outlet-indexing structures each include at least one keying pin receiving area positioned relative to said valve aperture and sized to receive the at least one keying pin.

3. The medical gas outlet system of claim 2 in which the at least one keying pin of the first gas-specific structure is a single latch pin, wherein said at least one keying pin receiving area of said first gas-specific outlet-indexing structure is a single latch pin receiving opening.

4. The medical gas outlet system of claim 3, wherein said latch pin receiving opening has a cross-sectional geometry and a spacing from said valve aperture that is unique to the specific gas types and corresponds to the single latch pin.

5. The medical gas outlet system of claim 3 in which the single latch pin includes a recess, further comprising a latch bar for engaging the recess to hold the first adapter in said valve aperture.

6. The medical gas outlet system of claim 5 further comprising a latch release mechanism for disengaging said latch bar from said recess in the latch pin.

7. The medical gas outlet system of claim 6, wherein said latch release mechanism includes a latch release member for urging said latch bar to disengage said latch bar from said recess in the latch pin.

8. The medical gas outlet system of claim 7, wherein said latch release mechanism further includes a release button for urging said latch release member.

9. The medical gas outlet system of claim 2 in which the at least one keying pin of the second gas-specific structure is a pair of keying lugs, wherein said at least one keying pin receiving area of the second gas-specific outlet-indexing structure is a pair of keying cavities.

10. The medical gas outlet system of claim 9, wherein said pair of keying cavities are uniquely positioned relative to each other for each specific gas types and correspond to the pair of keying lugs.

11. The medical gas outlet system of claim 9 in which the nose of each of the second adapter types includes at least one recess, further comprising a latch spring for engaging the at least one recess to hold the second adapter types in said valve aperture.

12. The medical gas outlet system of claim 11, further comprising a latch release mechanism for urging said latch spring to disengage said latch spring from the at least one recess.

13. The medical gas outlet system of claim 12, wherein said latch release mechanism comprises a cam for urging said latch spring to disengage said latch spring from said at least one recess.

14. The medical gas outlet system of claim 13, wherein said latch release mechanism includes a latch release member for urging said cam.

15. The medical gas outlet system of claim 14, further comprising a release button for urging said latch release member.

* * * * *